United States Patent [19]

Adachi et al.

[11] Patent Number: 4,562,256

[45] Date of Patent: Dec. 31, 1985

[54] 1,6-DIALKYL-3-SUBSTITUTED-4-NITROPHENYL-4,7-DIHYDROPYRAZOLO[3,4-B]PYRIDINE-5-CARBOXYLIC ACID ESTERS

[75] Inventors: Ikuo Adachi, Osaka; Teruo Yamamori, Hyogo; Motohiko Ueda; Masami Doteuchi, both of Osaka, all of Japan

[73] Assignee: Shionogi & Co., Ltd., Osaka, Japan

[21] Appl. No.: 641,822

[22] Filed: Aug. 17, 1984

[30] Foreign Application Priority Data

Sep. 8, 1983 [JP] Japan .................. 58-166258

[51] Int. Cl.$^4$ ........................... C07D 471/04
[52] U.S. Cl. .................................... 546/120
[58] Field of Search .......................... 546/120

[56] References Cited

FOREIGN PATENT DOCUMENTS 0114273  8/1984  European Pat. Off. ........... 546/120

*Primary Examiner*—Henry R. Jiles
*Assistant Examiner*—Barbara Cassatt
*Attorney, Agent, or Firm*—Wenderoth, Lind & Ponack

[57] ABSTRACT

1,6-Dialkyl-3-substituted-4-nitrophenyl-4,7-dihydropyrazolo[3,4-b]pyridine-5-carboxylic acid esters as Ca blocker having potent antihypertensive and coronary vasodilating actions and useful in treatment of diseases in circulatory system such as angina pectoris, hypertension, cerebrovascular dysfunction, arrhythmia, etc. with no systole inhibitory action, prepared from nitrobenzylideneacetoacetic acid esters on reaction with 3-substituted-5-amino-1-alkylpyrazoles.

5 Claims, No Drawings

1,6-DIALKYL-3-SUBSTITUTED-4-NITROPHENYL-4,7-DIHYDROPYRAZOLO[3,4-B]PYRIDINE-5-CARBOXYLIC ACID ESTERS

A. BRIEF SUMMARY OF THE INVENTION

The present invention relates to 4,7-dihydropyrazolo[3,4-b]pyridine derivatives.

More minutely the present invention relates to 4,7-dihydropyrazolo[3,4-b]pyridine derivatives represented by the general formula (I):

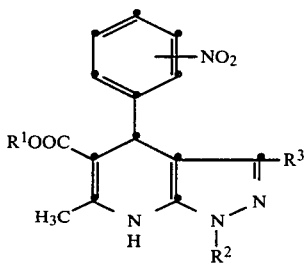

[wherein $R^1$ is $C_1$–$C_4$ alkyl,
$R^2$ is $C_1$–$C_4$ alkyl,
$R^3$ is $C_2$–$C_6$ alkenyl, $C_4$–$C_6$ cycloalkenyl, $C_4$–$C_6$ cycloalkyl $C_1$–$C_4$ alkyl, $C_1$–$C_4$ alkoxy $C_1$–$C_4$ alkyl, $C_4$–$C_6$ cycloalkyloxy $C_1$–$C_4$ alkyl, $C_5$–$C_6$ cycloalkyl containing oxo or protected oxo, 5 or 6 membered cycloalkyleneamino $C_1$–$C_4$ alkyl, $C_1$–$C_4$ haloalkyl, adamantyl, 1-methylpyrrolidinyl or 1,3-dithiolan-2-yl]
and production thereof, namely production of 4,7-dihydropyrazolo[3,4-b]pyridine derivatives represented by the general formula (I):

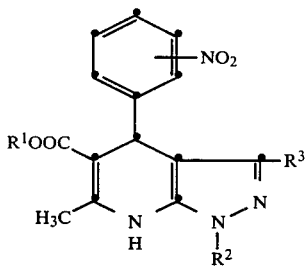

[wherein $R^1$, $R^2$ and $R^3$ each has the same meanings as defined above]
by the reaction of a compound represented by the general formula (II):

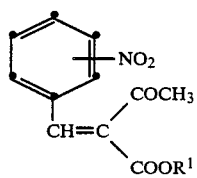

[wherein $R^1$ has the same meanings as defined above] with a compound represented by the general formula (III):

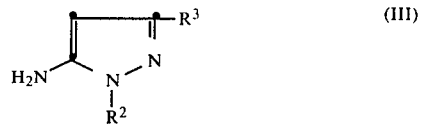

[wherein $R^2$ and $R^3$ each has the same meanings as defined above].

The compounds (I) of the present invention are classified into Ca-blockers having potent antihypertensive and coronary vasodilating actions and useful in treatment of diseases in circulatory system such as angina pectoris, hypertension, cerebrovascular dysfunction, arrhythmia, and so on. The compounds (I) have no systole inhibitory action as a side effect.

The compounds (I) of the present invention are prepared by the Michael addition of heterocyclic amines to α,β-unsaturated ketones accompanied by concurrent cyclization reaction. According to the process of this invention, aromatic condensed dihydropyridines as described in Japanese Patent Application No. 57-176763 by the present inventors can be prepared.

B. Prior art

The compounds having ca-blocking action have been utilized in treatment of diseases in circulatory system such as angina pectoris, hypertension, cerebrovascular dysfunction and so on, and Ca-blockers have been appreciated through their high therapeutic efficacy. Especially a series of compounds named 1,4-dihydropyridine derivatives has been investigated as Ca-blockers. As the known Ca-blockers, for example, nifedipine (U.S. Pat. No. 3,485,847), 1,4-dihydro-2,6-dimethyl-4-(2-nitrophenyl)-3,5-pyridine dicarbonic isobutylmethyl (Japanese Patent Publication No. 56-47185), 2-amino-1,4-dihydropyridine derivatives (Japanese Patent Publication No. 57-20306), 2-pyridyl-1,4-dihydropyridine derivatives (Japanese Unexamined Patent Publication No. 54-48796) and so on are exemplified. Concerning pyrazolodihydropyridine derivatives, their preparation and their Ca-blocking action, Japanese Patent Application No. 57-176763 by the present inventors are exemplified.

C. Detailed Description

In the above definition concerning general formula (I)–(III), the $C_1$–$C_4$ alkyl is straight or branched chain lower alkyl, including, for example, methyl, ethyl, propyl isopropyl, butyl, isobutyl, t-butyl and the like. The $C_2$–$C_6$ alkenyl is vinyl, 1-propenyl, allyl, isopropenyl, 1-butenyl, 2-butenyl, 3-butenyl, 2-pentenyl, 3-pentenyl, 2-hexenyl, 3-hexenyl or the like. The $C_4$–$C_6$ cycloalkenyl is 3-cyclopentenyl, 3-cyclohexenyl or the like. The $C_4$–$C_6$ cycloalkyl $C_1$–$C_4$ alkyl is $C_1$–$C_4$ alkyl substituted by $C_4$–$C_6$ cycloalkyl and the $C_4$–$C_6$ cycloalkyl is cyclobutyl, cyclopentyl, cyclohexyl or the like and the $C_1$–$C_4$ alkyl is that described above. The $C_1$–$C_4$ alkoxy $C_1$–$C_4$ alkyl is $C_1$–$C_4$ alkyl substituted by $C_1$–$C_4$ alkoxy and the $C_1$–$C_4$ alkoxy is methoxy, ethoxy, propoxy, isopropoxy, butoxy, isobutoxy, t-butoxy or the like and the $C_1$–$C_4$ alkyl is that described above. The $C_4$–$C_6$ cycloalkyloxy $C_1$–$C_4$ alkyl is $C_1$–$C_4$ alkyl substituted by $C_4$–$C_6$ cycloalkyloxy and the $C_4$–$C_6$ cycloalkyloxy is cyclobutyloxy, cyclopentyloxy, cyclohexyloxy or the like, and the $C_1$–$C_4$ alkyl is that described above. The $C_5$–$C_6$ cycloalkyl containing oxo or protected oxo is 2-oxocyclopentyl, 3-oxocyclopentyl, 3-oxocyclohexyl, 4-oxocyclohexyl, 1,4-dioxaspiro[4,5]decan-7-yl, 1,4-dioxaspiro[4,5]decan-8-yl or the like. The 5 or 6-membered cycloalkyleneamino $C_1$–$C_4$ alkyl is $C_1$–$C_4$ alkyl substituted by 5 or 6 membered cycloalkyleneamino and the cycloalkyleneamino is 1-pyrrolidinyl, 1-piperidinyl or the like and the $C_1$–$C_4$ alkyl is that described above. The $C_1$–$C_4$ haloalkyl is chloromethyl, 2-chloroethyl, 3-chloropropyl, 4-chlorobutyl, fluoromethyl, 2-fluoroethyl, 3-fluoropropyl, 4-fluorobutyl or the like.

The compound (I) of the present invention can easily be prepared by the reaction of the $\alpha,\beta$-unsaturated ketone reagents (II) with 5-aminopyrazole derivatives (III).

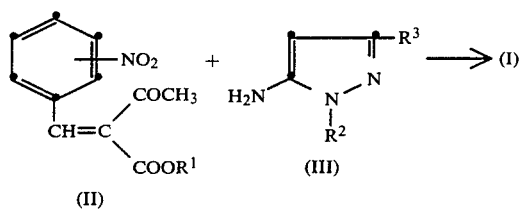

[wherein $R^1$, $R^2$ and $R^3$ each has the same meanings as defined above].

This reaction is carried out without or with a solvent. The solvent used in this reaction includes alcohols, e.g. methanol, ethanol, i-propanol, t-butanol and ethyleneglycol, hydrocarbons, e.g. benzene, toluene and xylene, ethers, e.g. ether, tetrahydrofuran, dioxane, glyme and diglyme, halogen ohydrocarbone, e.g. methylene chloride, chloroform, ethylene chloride and carbon tetrachloride, esters, e.g. ethyl acetate, or others, e.g. acetic acid, dimethylformaldehyde and pyridine. An acid or organic base may be used as a catalyst when necessary and the acid catalyst includes an inorganic acid such as sulfuric acid, hydrochloric acid, phosphoric acid and the like, an organic acid such as p-toluenesulfonic acid, acetic acid, formic acid and the like or a Lewis acid such as boron trifluoride, zinc chloride, aluminum chloride, magnesium chloride, stannous chloride and the like, and the organic base catalyst includes triethylamine, pyridine, pyrrolidine, piperidine and the like. The reaction terminates within a few hours to a few days at room temperature or under heating at 20°–100° C.

The starting materials for the reaction, 5-aminopyrazoles and $\alpha,\beta$-unsaturated ketones are made in the way shown below.

(1) Preparation of 5-aminopyrazoles (III)

5-Aminopyrazoles (III) can be made in the way shown in the following reaction scheme. The cyclization reaction of hydrazines (IV) with various $\beta$-ketonitriles (V) affords the title compounds in a good yield.

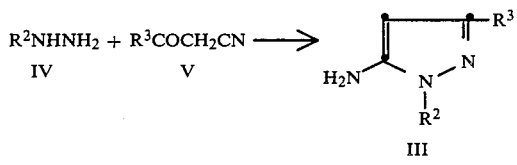

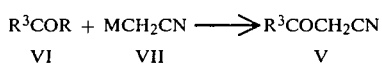

[wherein $R^2$ and $R^3$ each has the same meanings as defined above, R means halogen or ester residue, and M means alkali metal].

$\beta$-ketonitriles (V) are prepared by the reaction of acid chlorides or various esters with alkali metal salts of acetonitrile.

(2) Preparation of $\alpha,\beta$-unsaturated ketone reagents (II)

$\alpha,\beta$-Unsaturated ketones (II) are made by the condensation reaction of aldehydes (VIII) with acetoacetates (IX) according to the following reaction scheme [J. Chem. Soc., 81, 1212 (1902), Ann., 218, 170 (1883), J. Chem. Soc., 3092 (1962)].

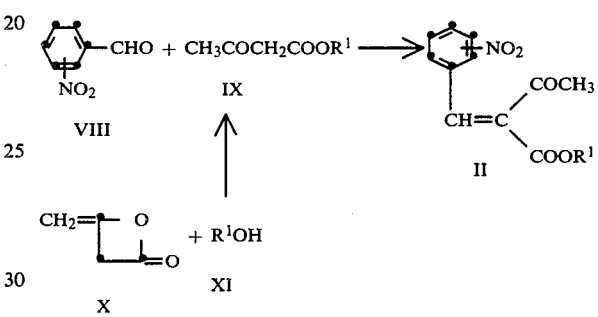

[wherein $R^1$ is that described above].

Acetoacetates (IX) are made by the reaction of diketene (X) with various alcohols (XI) in the presence of sulfuric acid catalyst.

The compounds (I) of this invention made from starting materials, 5-aminopyrazoles (III) and $\alpha,\beta$-unsaturated ketones reagent (II) as described above are exemplified below.

Methyl 3-allyl-1,6-dimethyl-4-(3-nitrophenyl)-4,7-dihydropyrazolo[3,4-b]pyridine-5-carboxylate, Methyl 3-(3-butenyl)-1,6-dimethyl-4-(3-nitrophenyl)-4,7-dihydropyrazolo[3,4-b]pyridine-5-carboxylate, Methyl 3-(3-cyclopentenyl)-1,6-dimethyl-4-(3-nitrophenyl)-4,7-dihydropyrazolo[3,4-b]pyridine-5-carboxylate, Methyl 3-(3-cyclohexenyl)-1,6-dimethyl-4-(2-nitrophenyl)-4,7-dihydropyrazolo[3,4-b]pyridine-5-carboxylate, Methyl 3-(3-cyclohexenyl)-1,6-dimethyl-4-(3-nitrophenyl)-4,7-dihydropyrazolo[3,4-b]pyridine-5-carboxylate, Methyl 3-cyclopentylmethyl-1,6-dimethyl-4-(2-nitrophenyl)-4,7-dihydropyrazolo[3,4-b]pyridine-5-carboxylate, Methyl 3-cyclopentylmethyl-1,6-dimethyl-4-(3-nitrophenyl)-4,7-dihydropyrazolo[3,4-b]pyridine-5-carboxylate, Methyl 1,6-dimethyl-3-(2-methoxyethyl)-4-(3-nitrophenyl)-4,7-dihydropyrazolo[3,4-b]pyridine-5-carboxylate, Methyl 3-cyclopentyloxymethyl-1,6-dimethyl-4-(3-nitrophenyl)-4,7-dihydropyrazolo[3,4-b]pyridine-5-carboxylate, Methyl 1,6-dimethyl-3-(1,4-dioxaspiro[4,5]decane-7-yl)-4-(3-nitrophenyl)-4,7-dihydropyrazolo[3,4-b]pyridine-5-carboxylate, Methyl 1,6-dimethyl-3-(1,4-dioxaspiro[4,5]decane-8-yl)-4-(3-nitrophenyl)-4,7-dihydropyrazolo[3,4-b]pyridine-5-carboxylate, Methyl 1,6-dimethyl-4-(3-nitrophenyl)-3-(3-oxocyclohexyl)-4,7-dihydropyrazolo[3,4-b]pyridine-5-carboxylate, Methyl 1,6-dimethyl-4-(3-nitrophenyl)-3-(4-oxocyclohexyl)-4,7-dihydropyrazolo[3,4-b]pyridine-5-carboxylate, Methyl 1,6-dimethyl-4-(3-nitrophenyl)-3-pyrrolidinomethyl-4,7-dihydropyrazolo[3,4-b]pyridine-5-carboxylate, Methyl 3-(4-chlorobutyl)-1,6-dimethyl-4-(3-nitrophenyl)-4,7-dihydropyrazolo[3,4-b]pyridine-5-carboxylate, Methyl 3-(1-adamantyl)-1,6-dimethyl-4-(3-nitrophenyl)-4,7-dihydropyrazolo[3,4-b]pyridine-5-carboxylate, Methyl 1,6-dimethyl-3-(1-methylprrolidin-2-yl)-4-(3-nitrophenyl)-4,7-dihydropyrazolo[3,4-b]pyridine-5-carboxylate, and Methyl 1,6-dimethyl-3-(1,3-dithiolan-2-yl)-4-(3-nitrophenyl)-4,7-dihydropyrazolo[3,4-b]pyridine-5-carboxylate.

Among the compounds described above of the present invention, the compounds containing protecting group can be converted into the corresponding deprotected compounds by deprotection. For example, ethylene ketals made in Examples 10 and 11 are hydrolyzed with dilute hydrochloric acid or dilute sulfuric acid in alcohol or dioxane to give the corresponding oxo derivatives (reference to Examples 17 and 18).

D. Effect

The compounds of the present invention have potent antihypertensive and coronary vasodilating actions based on Ca-blocking action and no systole inhibitory action which is one of the side effects, defects of the former Ca-blockers. The biological tests of the compounds shown below were preformed as follows. (The compounds)

(A): Nifedipine (B): Methyl 3-(3-cyclohexenyl)-1,6-dimethyl-4-(3-nitrophenyl)-4,7-dihydropyrazolo[3,4-b]pyridine-5-carboxylate (C): Methyl 3-cyclopentylmethyl-1,6-dimethyl-4-(3-nitrophenyl)-4,7-dihydropyrazolo[3,4-b]pyridine-5-carboxylate (D): Methyl 3-(3-cyclopentenyl)-1,6-dimethyl-4-(3-nitrophenyl)-4,7-dihydropyrazolo[3,4-b]pyridine-5-carboxylate (E): Methyl 3-(1,3-dithiolan-2-yl)-1,6-dimethyl-4-(3-nitrophenyl)-4,7-dihydropyrazolo[3,4-b]pyridine-5-carboxylate (Method of the experiment)

(1) Antihypertensive action

Female Spontaneously Hypertensive Rats (hereinafter abbreviated to SHR) whose systolic pressure was about 160 mmHg were used without anesthetization. After warming SHR at 50° C. for 2–3 minutes, the systolic pressure was measured indirectly by the tail-cuff method using a Physiograph and Electrosphygmomanometer (DMP-4B and PE-300, Narco Biosystems, Inc., Houston). Each compound was intraperitoneally administered to SHR at a dose of 3 mg/kg body weight.

(2) Coronary vasodilating action and systole inhibitory action

The guinea pigs (body weight: 400–800 g) of both sexes were hit hard on the head, and the carotid artery was cut and phlebotomized. The isolated heart was perfused at pressure of 50 cm $H_2O$ by the Langendorff method [Basic Pharmacology & Therapeutics, 9(4), 181 (1981)]. Krebs-Ringer bicarbonate solution containing 0.5% defibrinated blood at 27° C. was used as perfusate, into which a mixture of 95% oxygen and 5% carbon dioxide was introduced continuously. The perfusion flow was led into a drop counter, and its increase or decrease was regarded as an indication of coronary vasodilation or vasoconstriction; the isometric contraction of apex was recorded along with the drop number of coronary perfusate on a Recticorder (RJG 3006, Nihon Koden) by way of an F-D pick-up (SB-1T, Nihon Koden). Each compound was administered through a rubber tube connected with an aortic cannula at a dose of 0.1 μg.

TABLE 1

(Result)
Antihypertensive action, coronary vasodilating action and systole inhibitory action

| Compounds | Maximum Hypertension (mmHg) | Duration of Effect (hours) | Perfusion Flow Change (%) | Change of Contractile Tension (%) |
|---|---|---|---|---|
| (A) | 45 | 6 | +38 | −15 |
| (B) | 40 | 6 | +13 | 0 |
| (C) | 35 | 6 | +36 | 0 |
| (D) | 60 | 6 | +15 | 0 |
| (E) | 38 | 6 | +15 | 0 |

In consideration of the results shown above, the compounds of the present invention have distinctly potent antihypertensive and coronary vasodilating actions but no systole inhibition action so that the compounds can be utilized as drugs acting on the circulatory system with fewer side effects for men or animals.

The compounds of the present invention can be orally or parenterally administered to men or animals and formulated into various dosage forms according to the administering method. For example, tablets, capsules, pills, granules, fine granules, aqueous solution, emulsion and so on can be prepared. In the pharmaceutical preparation, usual conventional carriers or diluents, such as lactose, sucrose, starch, cellulose, talc, magnesium stearate, magnesium oxide, calcium sulfate, powdered gum arabic, gelatin, sodium arginate, sodium benzoate, stearic acid, and the like can be used. As injection, a solution in water for injection, saline solution, Ringer solution, and so on, or a suspension in sesame oil can be used.

The compounds of the present invention may be administered at a dose of about 1–50 mg a day for an adult in oral administration and at a dose of about 0.5–20 mg in intraveneous injection.

The present invention will be explained in the following Examples and Reference examples.

EXAMPLE 1

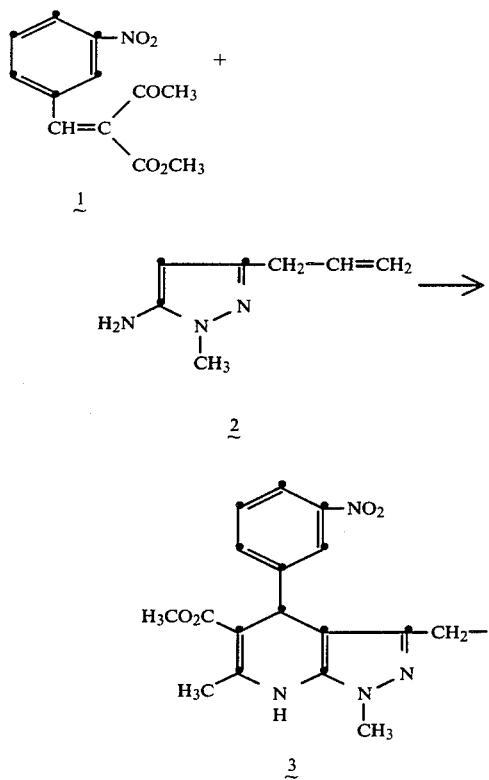

Preparation of methyl.3-allyl-1,6-dimethyl-4-(3-nitrophenyl)-4,7-dihydropyrazolo[3,4-b]pyridine-5-carboxylate A solution of 0.92 g (3.7 mM) of methyl.3-nitrobenzylideneacetoacetate 1 and 0.51 g (3.7 mM) of 3-allyl-5-amino-1-methylpyrazole 2 in 5 ml of t-butanol is heated at 80° C. in nitrogen atmosphere for 3 hours. After evaporation under reduced pressure, the resulting residue is dissolved in chloroform and the solution is washed with an aqueous sodium chloride solution, dried on magnesium sulfate and evaporated. The residue is chromatographed on a column of siliva gel and eluted with benzene-ethyl acetate (1:1) to give 1.1 g of the titled compound as yellow crystals. Recrystallization from ether gives 0.8 g of yellow prisms in 59.6% yield, mp 102°–105° C.

IR: $\nu_{max}^{Nujol}$ 3220, 1690, 1348 cm$^{-1}$.

NMR: $\delta^{CDCl_3}$ 2.39, 3.58, 3.68 (3H×3, s), 2.99 (2H, m), 4.92 (2H, m), 5.20 (1H, s), 5.74 (1H, s), 7.11–8.06. (5H, m).

Elementary Analysis: Calcd (%) for $C_{19}H_{20}N_4O_4$: C, 61.94; H, 5.47; N, 15.21.

Found (%): C, 61.85; H, 5.68; N, 14.94.

EXAMPLE 2–16

The compounds in Table 2 can be made in the same way as in Example 1. The physical constant, elemental analysis and IR and NMR spectra of each products are described in Tables 3 and 4.

TABLE 2

| Example | R' | R¹ | R³ | Location of NO₂ | Yield (%) |
|---|---|---|---|---|---|
| 2 | CH₃ | CH₃ | —CH₂CH₂CH=CH₂ | 3 | 93.6* |
| 3 | " | " | (cyclopentenyl) | " | 78.7 |
| 4 | " | " | (cyclohexenyl) | 2 | 70.1 |
| 5 | " | " | " | 3 | 81.7 |
| 6 | " | " | —CH₂-(cyclopentenyl) | 2 | 67.2* |
| 7 | " | " | " | 3 | 81.9 |
| 8 | " | " | —CH₂CH₂OCH₃ | " | 54.2 |
| 9 | " | " | —CH₂O-(cyclopentyl) | " | 82.7 |
| 10 | " | " | (dioxane derivative) | " | 24.7* |
| 11 | " | " | (dioxaspiro derivative) | " | 69.4 |
| 12 | " | " | —CH₂—N(cyclic) | " | 79.3* |
| 13 | " | " | —(CH₂)₄Cl | " | 36.9* |
| 14 | " | " | (adamantyl) | " | 68.1 |

TABLE 2-continued

| Example | R' | R¹ | R³ | Location of NO₂ | Yield (%) |
|---|---|---|---|---|---|
| 15 | " | " | ![pyrrolidine-N-CH₃ group] | " | 21.5 |
| 16 | " | " | ![dithiolane-isopropyl group] | " | 33.0* |

*hydrochloride

TABLE 3

| Example | appearance | solvent for recrystallization | m.p. (°C.) | molecular formula | Calcd. C | Calcd. H | Calcd. N | Found C | Found H | Found N |
|---|---|---|---|---|---|---|---|---|---|---|
| 2 | YP | ethanol | 170–174 (d) | $C_{20}H_{22}N_4O_4 \cdot HCl$ | 57.35 | 5.54 | 13.38 | 57.25 | 5.47 | 13.27 |
| 3 | YP | isopropanol | 181–183 | $C_{21}H_{22}N_4O_4$ | 63.94 | 5.62 | 14.21 | 64.01 | 5.50 | 13.93 |
| 4 | YP | ethanol | 215–217 | $C_{22}H_{24}N_4O_4$ | 64.69 | 5.92 | 13.72 | 64.61 | 5.82 | 13.50 |
| 5 | YP | ethyl acetate | 195–197 | $C_{22}H_{24}N_4O_4$ | 64.69 | 5.92 | 13.72 | 64.61 | 5.70 | 13.74 |
| 6 | P | acetone | 165–170 | $C_{22}H_{26}N_4O_4 \cdot HCl$ | 59.12 | 6.09 | 12.53 | 58.84 | 5.99 | 12.35 |
| 7 | YP | ethylacetate hexane | 159–160 | $C_{22}H_{26}N_4O_4$ | 64.37 | 6.39 | 13.65 | 64.44 | 6.39 | 13.62 |
| 8 | YP | ethyl acetate | 157–158 | $C_{19}H_{22}N_4O_5$ | 59.06 | 5.74 | 14.50 | 58.91 | 5.71 | 14.39 |
| 9 | YP | ethyl acetate | 174–175 | $C_{22}H_{26}N_4O_5$ | 61.96 | 6.15 | 13.14 | 61.80 | 6.17 | 12.93 |
| 10 | P | acetone | 188–189 | $C_{24}H_{28}N_4O_6 \cdot HCl$ | 57.20 | 5.60 | 11.12 | 57.07 | 5.80 | 11.02 |
| 11 | YL | | | | | | | | | |
| 12 | YP | methanol | 226–230 (d) | $C_{21}H_{25}N_5O_4 \cdot HCl$ | 56.31 | 5.85 | 15.54 | 56.12 | 5.83 | 15.59 |
| 13 | YP | acetone | 159–161 | $C_{20}H_{23}ClN_4O_4 \cdot HCl$ | 52.76 | 5.31 | 12.30 | 52.67 | 5.10 | 12.27 |
| 14 | YP | ether | 227–230 | $C_{26}H_{30}N_4O_4$ | 67.51 | 6.54 | 12.11 | 67.38 | 6.75 | 11.91 |
| 15 | YP | ethyl acetate | 158–160 | $C_{21}H_{25}N_5O_4$ | 61.30 | 6.12 | 17.02 | 60.94 | 6.24 | 16.68 |
| 16 | YN | methanol | 146–150 | $C_{19}H_{20}N_4O_4S_2 \cdot HCl$ | 48.66 | 4.51 | 11.95 | 48.66 | 4.81 | 12.01 |

YP = yellow prisms,
P = colorless prisms
YN = yellow needles,
YL = yellow liquid
(d) = decomposition point

TABLE 4

| Example | IR:$\nu^{Nujol}$(cm⁻¹) NH | CO | NO₂ | NMR: $\delta^{CDCl_3}$ |
|---|---|---|---|---|
| 2 | 3430 | 1690 | 1345 | 2.16(2H,m),2.38,3.57,3.66(3Hx3,s),4.87(2H,m),5.24(1H,s),5.69(1H,m),7.35–8.11(5H,m) |
| 3 | 3380 | 1700 | 1345 | 2.63(4H,m),2.38,3.59,3.68(3Hx3,s),3.08(1H,m),5.23(1H,s),5.60(2H,s),6.92(1H,br.s),7.33–8.11(4H,m) |
| 4 | 3310 | 1670 | 1355 | 1.66(3H,m),2.36,3.48,3.68(3Hx3,s),2.85(1H,m),5.61(2H,m),5.86(1H,s),6.84(1H,br.s),7.09–7.76(4H,m) |
| 5 | 3340 | 1695 | 1345 | 1.86(3H,m),2.39,3.59,3.69(3Hx3,s),5.28(1H,s),5.66(2H,m),6.94(1H,br.s),7.35–8.10(4H,m) |
| 6 | 2400 | 1683 | 1355* | 0.91–1.83(9H,m),2.40(3H,s),2.70(2H,m),3.58(3H,s),3.67(3H,s),5.22(1H,s),7.13–8.03(4H,m) |
| 7 | 3350 | 1700 | 1350 | 0.78–2.05(9H,m),2.19(2H,m),2.40,3.57,3.66(3Hx3,s),5.22(1H,s),6.82(1H,br.s),7.35–8.13(4H,m) |
| 8 | 3270 | 1690 | 1345 | 2.40,3.24,3.58,3.65(3Hx4,s),2.49(2H,t),3.40(2H,m),5.27(1H,s),7.00(1H,br.s),7.73(4H,m) |
| 9 | 3225 | 1690 | 1345 | 1.59(8H,m),2.43,3.54,3.66(3Hx3,s),3.86(1H,m),4.01(2H,m),5.30(1H,s),6.52(1H,br.s),7.74(4H,m) |
| 10 | 3430 | 1690 | 1350 | 0.82–3.02(9H,m),2.40,3.57,3.67(3Hx3,s),3.93(4H,s),5.25(1H,s),6.70(1H,br.s),7.13–8.08(4H,m) |
| 11 | 3430 | 1690 | 1350 | 1.10–2.55(9H,m),2.39,3.57,3.66(3Hx3,s),3.87(4H,s),5.25(1H,s),6.93(1H,br.s),7.31–8.13(4H,m) |
| 12 | 3430 | 1690 | 1350 | 1.72(4H,m),2.38(4H,m),2.40,3.53,3.65(3Hx3,s),3.18(2H,s),5.28(1H,s),7.18–8.08(5H,m) |
| 13 | | 1750 | 1350* | 1.64(4H,m),2.31(2H,m),2.43,3.62,3.72(3Hx3,s),3.54(2H,m),5.27(1H,s),7.72(5H,m) |
| 14 | 3350 | 1705 | 1348 | 1.27–2.05(15H,m),2.33,3.66,3.71(3Hx3,s),5.45(1H,s),6.83(1H,br.s),7.17–8.08(4H,m) |
| 15 | 3240 | 1685 | 1350 | 1.60(4H,m),2.07,2.39,3.54,3.67(3Hx4,s),3.00(3H,m),5.28(1H,s),6.72(1H,br.s)7.10–8.05(4H,m) |
| 16 | 3420 | 1690 | 1350 | 2.37,3.59,3.69(3Hx3,s),3.27(4H,m),5.23(1H,s),7.27–8.13(5H,m) |

*hydrochloride

EXAMPLE 17

Preparation of methyl 1,6-dimethyl-4-(3-nitrophenyl)-3-(3-oxocyclohexyl)-4,7-dihydropyrazolo[3,4-b]pyridine-5-carboxylate

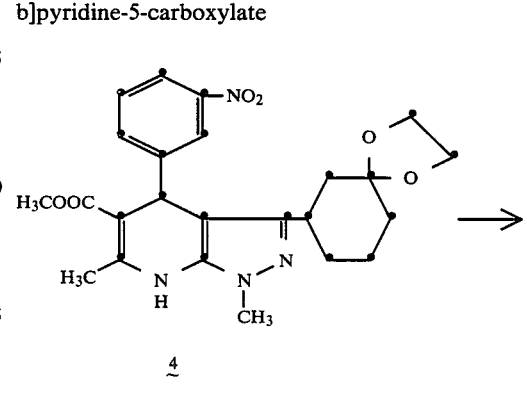

4

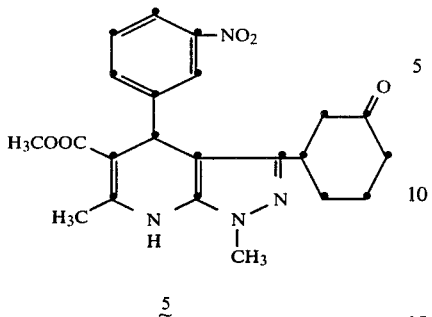

5

To a solution of 0.15 g (0.32 mM) of methyl 1,6-dimethyl-3-(1,4-dioxaspiro[4,5]decan-7-yl)-4-(3-nitrophenyl)-4,7-dihydropyrazolo[3,4-b]pyridine-5-carboxylate 4 in 1 ml of dioxane is added 0.5 ml of 10% hydrochloric acid and the mixture is stirred in nitrogen atmosphere for 20 hours. After evaporation under reduced pressure, the resulting residue is dissolved in methylene chloride and the solution is washed with dilute aqueous sodium hydrogencarbonate and then with water, dried on magnesium sulfate and evaporated. The residue is chromatographed on a column of silica gel and eluted with methylene chloride-ethyl acetate (1:1) to give 0.097 g of the titled compound as an yellow oil in 73.3% yield.

IR: $\nu_{max}^{CDCl_3}$ 3430, 1705, 1355 cm$^{-1}$.

NMR: $\delta^{CDCl_3}$ 0.95–2.92 (9H, m), 1.39, 3.57, 3.67 (3H×3, s), 5.24 (1H, s), 7.20–8.13 (5H, m).

On treatment with HCl/ether, 0.097 g of the above compound is made into the hydrochloride which on recrystallization from acetone gives 0.056 g of colorless prisms, mp 162°–164° C.

Elementary Analysis: Calcd (%) for C$_{22}$H$_{24}$N$_4$O$_5$: C, 57.33; H, 5.47; N, 12.16;

Found (%): C, 57.23; H, 5.36; N, 11.82.

EXAMPLE 18

Preparation of methyl 1,6-dimethyl-4-(3-nitrophenyl)-3-(4-oxocyclohexyl)-4,7-dihydropyrazolo[3,4-b]pyridine-5-carboxylate

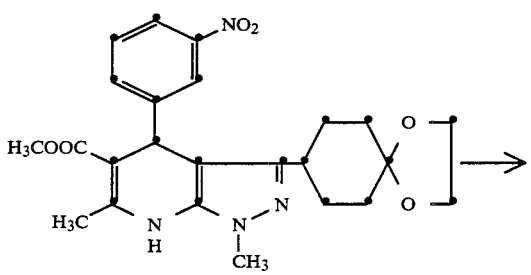

6

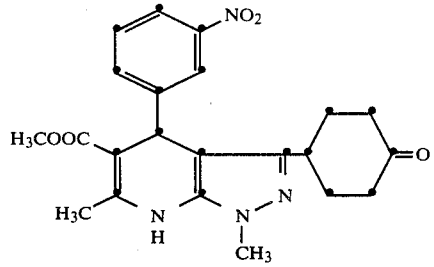

7

The titled compound can be made in the same way as in Example 17 in 95.1% yield as the hydrochloride, colorless prisms mp 174°–175° C. (decomposition)

Elementary Analysis: Calcd (%) for C$_{22}$H$_{24}$N$_4$O$_5$·HCl·1/2H$_2$O c, 56.23; H. 5.58; N, 11.92.

Found (%) C, 56.13; H, 5.65; N, 11.64.

IR: $\nu_{max}^{CDCl_3}$ 3425, 1700,1350 cm$^{-1}$.

NMR: $\delta^{CDCl_3}$ 1.43–2.87 (9H, m), 2.43, 3.59, 3.70 (3H×3, s), 5.29 (1H, s), 6.73 (1H, br, s), 7.30–8.12 (4H, m).

EXAMPLE 19

| Composition (tablet) | |
|---|---|
| Methyl 3-(3-cyclohexenyl)-1,6-dimethyl-4-(3-nitrophenyl)-4,7-dihydropyrazolo[3,4-b]pyridine-5-carboxylate | 10 mg |
| cornstarch | 50 mg |
| gelatin | 7.5 mg |
| Avicel (microcrystalline cellulose) | 25 mg |
| magnesium stearate | 2.5 mg |
| Total | 95 mg |

The composition is made into one tablet.

REFERENCE EXAMPLE 1

(i) Preparation of 5-amino-3-(3-cyclohexenyl)-1-methylpyrazole

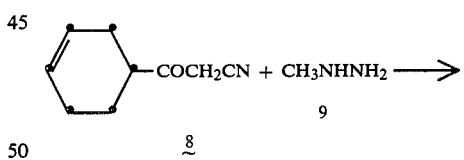

8   9

10

A solution of 1.91 g (12.8 mM) of 3-cyclohexenylcarbonylacetonitrile 8 and 0.7 ml (13.1 mM) of methylhydrazine 9 in 2 ml of ethanol is stirred at room temperature for 20 hours and evaporated under reduced repressure. The resulting residue is recrystallized from isopropyl ether to give 1.73 g of the titled compound as light yellow prisms in 75.0% yield, mp 146°–148° C.

NMR: δ$^{CDCl_3}$ 1.45–2.53 (6H, m), 2.75 (1H, m), 3.58 (3H, s),
3.72 (2H, bs), 5.36 (1H, s), 5.63–5.80 (2H, m).

(ii) Preparation of 3-cyclohexenylcarbonylacetonitrile

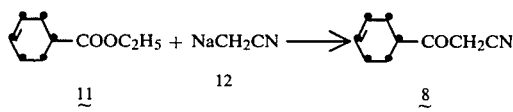

To a suspension of 1.25 g (2.60 mM) of 50% sodium hydride in 10 ml of toluene is added dropwise a solution of 2.01 g (1.30 mM) of ethyl 3-cyclohexenylcarboxylate 11 and 0.96 g (2.34 mM) of acetonitrile in 4 ml of toluene under nitrogen atmosphere in an hour and the mixture is stirred at 85° C. for 8 hours. After cooling, ice-cold water is added to the mixture. The aqueous phase is separated, washed with toluene, made acid with 10% hydrochloric acid and extracted with toluene. The extracted solution is washed with a dilute aqueous sodium hydrogencarbonate, and then with water, dried on magnesium sulfate and evaporated under reduced pressure. The resulting residue is chromatographed over silica gel and eluted with chloroform to give 1.91 g of the titled compound 8 as an yellow oil in 98.4% yield, NMR: δ$^{CDCl_3}$ 1.38–2.48 (6H, m), 2.80 (1H, m), 3.60 (2H, s), 5.50–5.80 (2H, m).

Reference Example 2-14

The compounds in Table 5 can be made in the same way as in Reference example 1.

TABLE 5

| Reference | $R^2$ | $R^3$ | Yield (%) | m.p. (°C.) | NMR: δ$^{CDCl_3}$ |
|---|---|---|---|---|---|
| 2 | $CH_3$ | —$CH_2CH=CH_2$ | 16.3 | 52–55 | 3.23(2H,m),3.57(3H,s),3.62(2H,br.s),5.09(2H,m),5.33(1H,s),5.99(1H,m) |
| 3 | " | —$CH_2CH_2CH=CH_2$ | 48.1 | | 2.42(4H,m),3.52(3H,s),3.58(2H,br.s),4.99(2H,m),5.27(1H,s),5.82(1H,m) |
| 4 | " | (cyclopentenyl) | 59.3 | 102–105 | 2.23—2.95(4H,m),3.17–3.82(3H,m),3.57(3H,s),5.35(1H,s),5.71(2H,s) |
| 5 | " | (cyclohexyl) | 64.9 | 106–107 | 0.93–2.32(9H,m),2.47(2H,m),3.51(3H,s),3.60(2H,br.s),5.28(1H,s) |
| 6 | " | —$CH_2CH_2OCH_3$* | 80.7 | | 2.73(2H,t),3.60,3.55(3H × 2,s),3.60(2H,t),3.47(2H,br.s),5.35(1H,s) |
| 7 | " | —$CH_2$—O—(cyclopentyl) | 24.6 | 112–114 | 1.38–1.90(8H,m),3.47(2H,br.s),3.60(3H,s),4.00(1H,m),4.31(2H,s),5.55(1H,s) |
| 8 | " | (cyclohexyl with dioxolane) | 42.0 | 133–138 | 1.03–2.20(8H,m),2.77(1H,m),3.55(2H,br.s)3.57(3H,s),3.90(4H,s),5.28(1H,s) |
| 9 | " | (cyclohexyl with dioxane) | 75.6 | 167–177 | 1.33–2.05(8H,m),2.55(1H,m),3.57(3H,s),3.71(2H,br.s),3.94(4H,s)5.36(1H,s) |
| 10 | " | —$CH_2$—N(pyrrolidine)* | 49.5 | | 1.65–2.10(4H,m),2.82–3.25(4H,m)3.62(3H,s),5.68(1H,s),6.87(2H,br.s) |
| 11 | " | —$(CH_2)_4$—Cl* | 56.7 | | 1.53–2.05(4H,m),2.49(2H,m),3.52(4H,m),3.53(3H,s),5.30(1H,s) |
| 12 | " | (adamantyl) | 89.5 | 190–191 | 1.65–2.15(15H,m),3.40(2H,br.s),3.60(3H,s),5.38(1H,s) |

TABLE 5-continued

| Reference | R² | R³ | Yield (%) | m.p. (°C.) | NMR: $\delta^{CDCl_3}$ |
|---|---|---|---|---|---|
| 13 | " | ![pyrrolidinyl with N-CH3] | 54.7 | 138–139 | 1.48–2.48(5H,m),2.24,3.58(3H × 2,s),3.10(2H,m),3.53(2H,br.s),5.47(1H,s) |
| 14 | " | ![1,3-dithiolane] | 49.5 | 77–80 | 3.17–3.77(6H,m),3.56(3H,s),5.33(1H,s),5.60(1H,s) |

*oil

What we claim is:

1. A 4,7-dihydropyrazolo[3,4-b]pyridine derivative represented by the general formula:

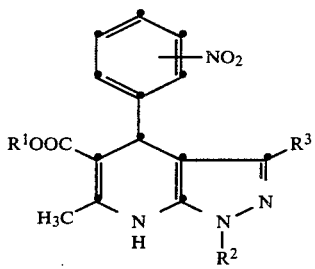

[wherein
R¹ is $C_1$–$C_4$ alkyl,
R² is $C_1$–$C_4$ alkyl,
R³ is $C_2$–$C_6$ alkenyl, $C_4$–$C_6$ cycloalkenyl, $C_4$–$C_6$ cycloalkyl $C_1$–$C_4$ alkyl, $C_1$–$C_4$ alkoxy-$C_1$–$C_4$ alkyl, $C_4$–$C_6$ cycloalkyloxy $C_1$–$C_4$ alkyl, $C_5$–$C_6$ cycloalkyl containing oxo or protected oxo, 5 or 6 membered cycloalkylene-amino $C_1$–$C_4$ alkyl, $C_1$–$C_4$ haloalkyl, adamantyl, 1-methylpyrrolidinyl or 1,3-dithiolan-2-yl]
and the acid addition salt thereof.

2. A compound claimed in claim 1, that is, methyl 3-(3-cyclohexenyl)-1,6-dimethyl-4-(3-nitrophenyl)-4,7-dihydropyrazolo[3,4-b]pyridine-5-carboxylate.

3. A compound claimed in claim 1, that is, methyl 3-cyclo-pentylmethyl-1,6-dimethyl-4-(3-nitrophenyl)-4,7-dihydro-pyrazolo[3,4-b]pyridine-5-carboxylate.

4. A compound claimed in claim 1, that is, methyl 3-(3-cyclo-pentenyl)-1,6-dimethyl-4-(3-nitrophenyl)-4,7-dihydropyrazolo-[3,4-b]pyridine-5-carboxylate.

5. A compound claimed in claim 1, that is, methyl 3-(1,3-dithioran-2-yl)-1,6-dimethyl-4-(3-nitrophenyl)-4,7-dihydro-pyrazolo[3,4-b]pyridine-5-carboxylate.

* * * * *